US006897241B2

(12) United States Patent
Frome

(10) Patent No.: US 6,897,241 B2
(45) Date of Patent: *May 24, 2005

(54) PREPARATION OF TOPICAL REGIONAL COMPOSITIONS FOR THE RELIEF OF PAIN

(76) Inventor: Bruce M. Frome, P.O. Box 15157, Beverly Hills, CA (US) 90209-1157

( * ) Notice: Subject to any disclaimer, the term of this patent is extended or adjusted under 35 U.S.C. 154(b) by 0 days.

This patent is subject to a terminal disclaimer.

(21) Appl. No.: 10/143,320

(22) Filed: May 9, 2002

(65) Prior Publication Data

US 2003/0060463 A1 Mar. 27, 2003

Related U.S. Application Data

(62) Division of application No. 09/569,515, filed on May 12, 2000, now Pat. No. 6,387,957, which is a division of application No. 08/531,760, filed on Sep. 22, 1995, now Pat. No. 6,197,830.

(51) Int. Cl.[7] .................... A61K 31/135; A61K 31/485
(52) U.S. Cl. ...................... 514/647; 514/289; 514/654
(58) Field of Search ............................... 514/647, 289, 514/654, 183

(56) References Cited

U.S. PATENT DOCUMENTS

| | | | |
|---|---|---|---|
| 2,676,177 A | 4/1954 | Schnider | 260/285 |
| 2,928,829 A | 3/1960 | Mull | 260/239 |
| 3,006,913 A | 10/1961 | Mull | 260/239 |
| 3,055,882 A | 9/1962 | Mull | 260/239 |
| 3,205,264 A | 9/1965 | Tristram | 260/570.3 |
| 3,254,124 A | 3/1966 | Stevens | 260/570.5 |
| 4,777,171 A | 10/1988 | Beitner | 514/225.5 |
| 5,258,386 A * | 11/1993 | Newman et al. | 514/289 |
| 5,260,313 A | 11/1993 | Frome | 514/552 |
| 5,366,980 A * | 11/1994 | Smith | 514/289 |
| 5,446,070 A | 8/1995 | Mantelle | 47/32 |
| 5,817,699 A | 10/1998 | Flores et al. | 31/135 |

FOREIGN PATENT DOCUMENTS

| | | | |
|---|---|---|---|
| DE | 4340767 * | 6/1995 | |
| EP | 0 431 663 A1 | 11/1990 | ......... A61K/31/645 |
| GB | 2074026 * | 10/1981 | |
| WO | WO 91/02527 | 3/1991 | .......... A61K/31/44 |
| WO | WO 92/14453 | 9/1992 | |
| WO | 95/22965 * | 8/1995 | |
| WO | WO 98/01157 | 1/1998 | |

OTHER PUBLICATIONS

Liu et al., Journal of Pharmacology and experimental therapeutics, (Oct., 1975) 195(1) 94–104 (abstract).*
Ebert et al., Neuroscience Letter, (1995) 187(3), pp. 165–168 (abstract).*
Embase Abstract, AN. 96229589, Lipman, A.G., "Analgesic drugs for neuropathic and sympathetically maintained pain", Clinics in Geriatric Medicine, 12:501–515 (1996).
Ortega–Alvaro, A. et al., "The Effects of Different Monoarminergic Antidepressants on the Analgesia Induced by Spinal Cord Adrenal medullary Transplants in the Formalin Test in Rats," Anesthesia and Analgesia, 84(4):816–820 (1997).
Sierralta, F. et al., "Effect of p–hlorophenylalanine and α–Methyltyrosine on the Antinociceptive Effect of Antidepressant Drugs," Pharmacology and Toxicology, 77(4):276–280 (1995).
Crowley, K.L. et al., "Clinical Application of Ketamine Ointment in the Treatment of Sympathetically Maintained Pain," Pharmaceutical Compounding, 2(2):122–127 (1998).
H. Willimann, P.Walde, P.L. Luisi et al., "Le cithin Organogel as Matrix for Transdermal Transport of Drugs", Journal of Pharmaceutical Sciences, V.81,Nr.9 Sep. 1992.
Gordon L. Flynn, General Intro. Topical and Transdermal Drug Delivery Systems Topical Drug Bioavailability, Bioequivalence, and Penetration, Plenum Press, 1993, Chapter 20, pp. 369–391.
O. Shimoda; T. Kano; Takaki, et al., "Transdermal application of 10% lidocaine–gel for management of pain associated with herpes zoster": Department of Anesthesiology, Kumamoto Rosai Hospital, Yatsushiro. Masui 1993 Aug.;42(B):1171–6, Abstract.

* cited by examiner

Primary Examiner—Phyllis G. Spivack
(74) Attorney, Agent, or Firm—Stephen E. Reiter; Foley & Lardner

(57) ABSTRACT

A method is presented for the preparation of topically applied compositions used for the treatment of regional pain, especially sympathetically mediated pain. NMDA receptor antagonists, such as ketamine or dextromethorphan, and one or more tricyclic antidepressants, such as amitriptyline, in combination, are employed.

15 Claims, No Drawings

PREPARATION OF TOPICAL REGIONAL COMPOSITIONS FOR THE RELIEF OF PAIN

RELATED APPLICATIONS

This application is a divisional application of U.S. patent application Ser. No. 09/569,515, filed May 12, 2000, now U.S. Pat. No. 6,387,757, which is a divisional of U.S. patent application Ser. No. 08/531,760, filed Sep. 22, 1995, now issued as U.S. Pat. No. 6,197,830, the contents of both of which are hereby incorporated by reference herein in their entirety.

BACKGROUND

1. Field of Invention

The field of this invention is the process for the preparation of topical compositions used for the treatment of pain, especially pain caused by nerve injury or sympathetically mediated pain. More specifically, the field of this invention relates to n-methyl d-aspartate (NMDA) receptor antagonists, anticholinergic agents, and sympathetic blocking agents, administered topically in a gel or cream base composition, and effective for the relief of pain due to nerve injury or damage.

Sympathetically mediated pain (SMP) is a type of pain in which overactivity of the sympathetic nervous system plays a crucial role. It includes the syndromes of reflex sympathetic dystrophy, causalgia, neuropathic pain secondary to nerve injury, and pain from neuromas. It encompasses all neurogenic pain that is not central and is related to a nerve injury regardless of the cause.

Sympathetically mediated pain (SMP) is a major worldwide epidemic condition. There are greater that 6 million Americans suffering from SMP today. SMP can be so severe that it has been compared to being ten times the intensity caused by childbirth. It is, overall, the most common cause of pain-induced suicide in the US. It is virtually incurable if treatment is initiated greater than 6 months after the disease has been triggered. However, diagnosis in these six months is unusual because, early in the condition, it is so difficult to make.

The signs and symptoms of sympathetically mediated pain are varied. It occurs most often in the limbs but virtually any part of the body can be affected. It can occur at any age, but is often unrecognizable in the very young and is rarely diagnosed at all in its early stage in the absence of a high degree of suspicion. A special bone scan called the triple phase bone scan is diagnostic in some cases in later stages.

There are a number of different types of pain associated with nerve injury or SMP. These types are usually defined by their subjective effects. The specific types of pains which are included in the field of this invention are defined as follows:

Allodynia: pain due to a stimulus that normally does not cause pain, for example as the light touch from air passing over skin.

Hyperpathia: A painful syndrome characterized by increased reaction to a stimulus, especially a repetitive stimulus, as well an increased threshold.

Hyperesthesia: An increased sensitivity to normal stimulation excluding the special senses.

Hyperalgesia: An increased response to a stimulus that is normally painful.

Dysesthesia: An unpleasant abnormal sensation, whether spontaneous or evoked.

Paresthesia: An abnormal Sensation, whether spontaneous or evoked.

Deafferentation Pain: Pain due to loss of sensory input into the central nervous system, as occurs with avulsion of the brachial plexus or other types of lesions of the peripheral nerves or due to pathology of the central nervous system.

Anesthesia Delorosa: Pain in an area or region that is anesthetic (anesthetic means absence of all sensations).

A classical patient with SMP exhibits hyperpathia, allodynia, swelling, and an electrical shock type parasthesia pain in the limbs. Many SMP patients also experience the other types of pain defined above. The compositions of this invention result in significant relief of all types of SMP defined above.

The field of this invention is the preparation of compositions utilized in the topical treatment of these types of pain.

2. Description of Prior Art

The prior and present treatment of sympathetically mediated pain (SMP) or pain due to nerve damage is directed towards relief of subjective symptoms. Currently, there are several categories of treatments utilized.

I. Oral Medication

1. Standard analgesic medications, including morphine and other opiates, which are generally almost completely ineffective for this type of pain.

2. Ganglionic blocking agents, such as phenoxybenzamine, are more effective than standard analgesics. However, in doses necessary to achieve even minimal pain relief, they can produce totally disabling side effects, such as a sufficiently sharp fall in the blood pressure to render the patient unable to stand or walk without fainting.

3. Tricyclic antidepressants, such as amitriptylline, are mildly effective in about 20% of cases but cause drowsiness.

4. Anti-convulsants, such as carbamazepine, are partially effective in about half of the cases in the relief of electric shock type lancinating parasthesia pain but offer little or no relief from the major burning type of pain.

5. Adrenergic blocking agents, such as yohimbine and terazosine, are only sporadically and temporarily effective. The low blood pressure caused by these agents make their use limited.

II. Nerve Blocks: Epidural nerve blocks or sympathetic nerve blocks, are invasive procedures using local anesthetics or nerve sclerosing agents, such as phenol or alcohol. Such nerve blocks temporarily or permanently interrupt nerve conduction to and from the painful area. The methods are invasive and temporary, although the analgesic affects may last as long as four to six weeks. However, these methods require a physician pain specialist to inject the patient and are usually performed in an expensive, often inconvenient, hospital setting. Injections using sclerosing agents are fraught with danger, including the formation of neuromas, which can result in worse pain than was originally present. Nerve sclerosing agents are tried as a last resort but rarely are successful.

III. Surgical Procedures: Many have been devised wherein the SMP patient would be subjected to a severing of the spinal cord or of nerves, and even ablation of parts of the brain. However, in the long term, these methods invariably end up with poor results and worse pain. Other surgical procedures costing upwards of 20 thousand dollars each include permanent implantation of peripheral nerve stimulators, spinal cord stimulators, and deep brain stimulators. Aside from being very expensive, these implants are risky and the results are poor.

IV. Topical Treatments: There are currently a limited number of topical treatments available. These agents offer only minimal and short term, usually less than one hour, of pain relief.

1. Geranium oil (applicant's U.S. Pat. No. 5,260,313): The severe pungent odor of strong geranium oil discourages frequent use of this medication. In addition, the relief is generally limited to 2 hours or less.
2. Topical local anesthetics or salicylates: Pain relief occurs in fewer than 25% of the SMP patients. Even then, only half of the pain is relieved.
3. Capsaicin (Cayenne Pepper Extract): This agent applied topically results in an initial burning sensation that discourages the SMP patient from its further use. It provides substantial pain relief for only a small number of SMP patients and then not until after one week of repetitive use.

V. Miscellaneous Other Methods: Although these techniques are occasionally successful, pain relief results in SMP is considered minimal. These methods include, but are not limited to, guided imagery techniques, acupuncture, hypnosis, physical therapy, and biofeedback.

BRIEF SUMMARY: OBJECTS AND ADVANTAGES

The object of the invention is to provide a process for the preparation of a composition that results in a relatively simple topical method of pain relief in patients with all types of pain, especially sympathetically mediated pain (SMP) or pain due to nerve damage, including peripheral neuropathies.

It is another object of the invention to provide a method of preparation of a composition that results in pain relief in SMP patients after the application of topical substances.

An additional object of the invention is to provide a composition for pain relief which will last longer than two hours. A further object of the invention is to provide a composition for pain relief which will last longer than 2 hours and which can be self-administered.

A still further object of the invention is to provide a method of preparation of this type of topical self administered pain relief utilizing non toxic agents with minimal side effects.

A yet further object of the invention to provide a method of preparation of this type of non-toxic, minimal side effect, topical medication for the treatment of patients with pain, especially nerve injury pain or sympathetically mediated pain, which is non-addictive and non-habit forming.

Still further objects and advantages will become apparent through a consideration of the ensuing description.

PREFERRED EMBODIMENT: DESCRIPTION AND OPERATION

The present invention relates to the methods of preparation of the compositions used as topical regional treatments for the purpose of eliminating pain, especially pain due to nerve damage (which is referred to as sympathetically mediated pains or SMP). These compositions contain as their principle and active therapeutic agent a drug from one (or more) of the following 3 classes of agents;

Class 1. The non-competitive n-methyl d-aspartate ion channel blocking agents, which will be referred to hereafter as NMDA receptor antagonists such as ketamine (U.S. Pat. No. 3,254,124) and dextromethorphan (U.S. Pat No. 2,676,177). Ketamine is currently used as a general anesthetic and primarily administered parenterally by injection. Dextromethorphan is used primarily as a cough suppressant Class 2. The anticholinergic agents, an example of which are tricyclic antidepressants such as amitriptylline (U.S. Pat. No. 3,205,264). Amitriptylline is currently primarily prescribed for the oral treatment of depression. It is secondarily prescribed for use as an oral analgesic. It is also available parenterally.

Chemical Structures

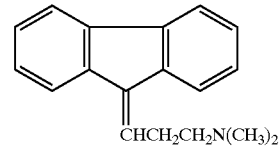

Amitriptyline

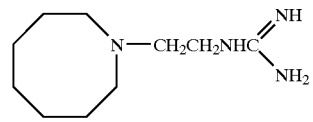

Guanethidine

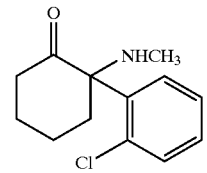

Ketamine

Class 3. Sympathetic blocking agents such as guanethidine. (U.S. Pat. Nos. 2,928,829, 3,006,913, and 3,055,882). This group of drugs is currently generally prescribed for the treatment of peripheral vascular disorders and hypertension. These agents are available by both the parenteral and oral routes.

None of the agents in any of the above three classes is currently available nor prescribed for use by topical administration.

Preparation of Topical Compositions:

To prepare a topical composition, one or more of the active therapeutic agents from the three classes above is directly mixed with a suitable topical base. The efficacious and used most commonly base in our studies is a lecithin matrix gel. The efficiency of lecithin, a matrix base, is attributed to its ability to enhance transport of the active therapeutic agent across the dermis and into the tissues below so as to exert the effects of these agents on the nerves in the region below where it is applied.

The main ingredients used to make the matrix gel are pure soybean lecithin granules and liquid octylpalmatate. The liquid octylpalmatate and ground lecithin are mixed at room temperature in a proportion of 60% lecithin to 40% octylpalmatate. For example, 1 kilogram of lecithin is added to 600 cc of octylpalmatate. This mixture is then placed in a large commercial-type blender and blended together to the point where the whole mixture becomes liquefied. Even though granules of lecithin will still be seen floating around in the mixture, the whole mixture should appear to be in an almost total liquid state. This liquid is then transferred to 500 cc beakers which are placed on standard magnetic stirrers and allowed to stir at half speed undisturbed for 24 hours. At the end of the 24 hours the remaining lecithin granules will have completely liquefied, leaving a dark brown homogenous liquid of light oily texture.

The active therapeutic agent is then added to the liquid gel. For example, injectable ketamine, 50 mg per ml, is added to the lecithin gel. For every 90 ml of the now liquefied lecithin, 10 ml of ketamine is added. By weight, the added 10 ml of ketamine equals 500 mg, resulting in 500 mg of ketamine per 100 cc of the 0.5% topical composition.

The liquefied lecithin tends to thicken and gel when additional water or other liquid is added, a reverse of the expected effect. As the 500 mg of ketamine is commercially delivered in a 10 cc liquid base, when it is added to the lecithin and stirred, the lecithin will begin to increase in density and gel. When a thicker gel is desired, water is added, a few milliliters at a time. The final thickness of the gel depends on how much additional water is added. The more water, the thicker the gel will become. In the example presented, the liquid ketamine is added so as to create a gel of optimal density for use by our patients. The end point or target density of the gel optimally is equal to that of commercial soft margarine.

In the preparation of a 0.05% tricyclic antidepressant (amitriptylline) lecithin composition, 5 ml of liquid injectable amitriptylline (10 mgm/ml) or five finely crushed 10 mgm amitriptylline tablets are utilized. The powdered tablets are placed in liquid solution by dissolving them in 2 cc of distilled water. The 5 ml of injectable liquid or dissolved tablets is then added to 95 ml of liquefied lecithin so as to make 100 cc of the topical amitriptylline composition. The method of preparation of the lecithin base for the amitriptylline topical composition is performed in the same manner as described in the preparation of the ketamine composition example above with the exception, naturally, of substituting the prescribed dosage of amitriptylline for ketamine.

In the preparation of a 0.05% guanethidine-lecithin composition five finely crushed 10 mgm guanethidine tablets are utilized. The powdered tablets are then dissolved in 5 cc of distilled water and added to 95 cc of lecithin liquid so as to prepare a 0.05% guanethidine-lecithin composition. The method of preparation of the guanethidine lecithin base is the same as described for the ketamine composition example above other than, naturally, substituting the prescribed dosage of guanethidine for ketamine in the composition.

Instead of the lecithin base, it is also possible to use 99% pure aloe vera gel or any standard, medicinal, or cosmetic base including, but not limited to, cocoa butter, aquafor, petroleum jelly and most cold creams. The oil-based gels, overall, have a more rapid onset of action as well as being more cosmetically palatable to the patients.

The concentrations of the active therapeutic agents described above were, overall, the most effective in our studies. However, other concentrations may be more effective or less effective for individual patients.

Method of Application:

In applying these compositions to the skin, for maximum effectiveness and increased absorption, the area to which the composition is to be applied is first cleansed with an astringent, such as a standard commercial antiseptic, alcohol or witchhazel astringent. The area is then allowed to dry for a few seconds. Next, the prepared topical composition is applied to the complete target area of the skin (the painful area) and gently, but firmly, massaged in with the fingertips until all visible gel or cream has been absorbed.

The volume of gel or cream utilized naturally depends on the surface area of the patient's pain. One to ten teaspoons may be utilized in order to obtain the desired pain relief. One teaspoon may be used for a smaller pain-affected area and up to ten teaspoons may be applied for larger pain-affected areas.

Response:

Typically, the initial application of any one of these compositions to any area of the body exhibiting pain produces an initial fleeting feeling of numbness, similar to a topical anesthetic being applied to the skin. No adverse effect will occur to either the patient or to the bare fingered applicator (if composition is not self-applied) when the 0.05% ketamine composition is used as the active therapeutic agent. When 0.05% amitriptylline is the active agent in the composition, the composition may produce a dryness of the mouth and some blurriness of vision. A person applying the topical cream or gel may be protected to avoid such dry mouth by wearing rubber gloves or a finger cot.

The guanethidine compositions occasionally result in headaches due to cerebral vasodilatation, and may occur in persons prone to migraines or vascular headaches (including any person applying the gel). Guanethidine gel must not be administered by migraine/vascular headache prone individuals unless they wear protective hand-covering. Furthermore, guanethidine gel or cream is relatively contraindicated in migraine/vascular headache prone patients or patients who are in shock, as the guanethidine may result in a severe headache and a significant lowering of blood pressure.

Mechanism of Action:

The mechanism of action of topical ketamine is believed to be similar to a long acting local anesthetic, thereby effectively blocking the underlying nerves. To date, however, the mechanism of action of topically applied ketamine acting regionally has not been fully determined.

The mechanism of action of the amitriptylline compositions is presumed to be due to the anticholinergic action of the tricyclic antidepressant. Once the antidepressant (or one of the other anticholinergics) passes through the dermis it acts by blocking acetylcholine, a neurotransmitter. This prevents the transmission of impulses in the A-delta and C pain fibers, thereby resulting in pain relief.

Guanethidine in the topical composition passes into underlying adrenergic neurons resulting in an adrenergic blockade to occur. This prevents the transmission of impulses in the A-delta and C pain fibers. The topical guanethidine further inhibits or interferes with the release or distribution of the chemical mediator (presumably norepinepherine) at the sympathetic neuro-effector junction.

Serum blood levels of patients treated with compositions containing the active agents, 0.5% ketamine, 0.05% amitriptylline, and 0.05% guanethidine, respectively, were done at 5, 15, 30, 45, 60, 120 minutes following application of the compositions to eight different sites on each patient's body. The size of the sites varied from smaller than a quarter to an area equal to the patients entire back. No detectable blood levels of any of the compounds were ever detected.

The general mode of action of these topically applied compositions is referred to as topical regional. This refers to their action, which is restricted to the region below the surface where the application has occurred. In using topical regional routes of administration, the volume of drug absorbed systemically is so minimal that there is never a detectable blood level with standard blood testing laboratory equipment.

Following application of the topical composition the duration of significant pain relief was determined to be 2 to 24 hours. The composition may be reapplied as needed when the pain returns. The duration of pain relief was not dependent upon the severity of the patient's symptoms prior to the application.

The study in the following pages further illustrates the present invention. It will be apparent to those skilled in the art that only the preferred embodiment has been described in the preceding and in the following example and that there are various modifications and alterations which fall within the scope of this invention and are intended to be covered by the claims appended hereto.

EXAMPLES

Study Comparing Efficacy of Topical Compositions Containing Therapeutically Active Agents on Relief of Sympathetically Mediated Pain Introduction The purpose of this study was to evaluate and compare the safety and efficacy in the application of five topical compositions prepared with three active ingredients and applied singly or in combinations for the purpose of relief of sympathetically mediated pain (SMP).

Materials and Methods

The study size was a total of thirty four volunteer subjects; fifteen female and nineteen male volunteer subjects. Their ages ranged from 29 to 84 with a mean of 52 years of age. All subjects were diagnosed with severe sympathetically mediated pain.

Three different therapeutically active agents were utilized, alone or in combination, in preparations of lecithin matrix gels. The contents of these compositions were as follows:

1. Placebo (with no active ingredients)
2. Compositions containing Ketamine 0.5%
3. Compositions containing Amitriptylline 0.05%
4. Compositions containing Guanethidine 0.05%
5. Compositions containing a combination of Ketamine 0.5% and Amitriptylline 0.05%
6. Compositions containing a combination of Ketamine 0.5% and Guanethidine 0.05%

A different composition was applied each treatment day to the area of maximum pain. The patients were asked to indicate the level of their pain immediately prior to the application of the compositions, and then at intervals of 5, 10, 15 minutes, 1, 2 and 3 hours after receiving treatment. Pain intensity was measured using the scale below.

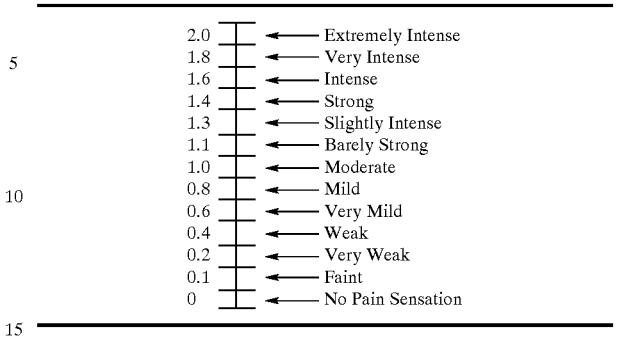

Each patient was asked to choose the word that best described how the pain felt. The number corresponding to that word was then used to tabulate the intensity of the pain and for statistical analysis.

2 characteristic types of sympathetically mediated pain were tested;

1. Pain at rest.
2. Response to light touch (allodynia, hyperaesthesia, hyperpathia). Light touch was measured by stroking the skin over the painful area with a cotton swab.

Patients were questioned as to their pain intensity at 5 minute intervals for 15 minutes and then at 1, 2 and 3 hours. SIGNIFICANT PAIN RELIEF WAS DEFINED AS >50% PAIN RELIEF SUSTAINED GREATER THAN 2 HOURS. For example, if a given patient rated his pain immediately prior to application of the compositions as "very intense", he would get a 1.8 score per the scale. In order for him to be placed in the category defined as "significant pain relief", he would have to judge his pain following application below 0.9, i.e., between "mild" and "no pain sensation" on the scale.

The entire study was performed under double blind conditions in that neither the subject nor the observers knew the contents of the topical compositions being applied. The study was conducted over five weeks with patients receiving treatment twice weekly with at least two days between treatments.

Topical Compositions Study: Summary of Results

Total number of patients treated: 34 patients
Average age of patients treated: 52 years of age

| Treatment | Percentage Patients with >50% Pain Relief | | | Percentage Patients with 0 Pain Relief | | | Time of Onset of Pain Relief (Patient Percentage) | | | Duration of >50% Pain Relief (Patient Percentage) | | |
|---|---|---|---|---|---|---|---|---|---|---|---|---|
| | At 5 Minutes | At 2 Hours | At 3 Hours | At 5 Minutes | At 2 Hours | At 3 Hours | 5 Minutes | 10 Minutes | >15 Minutes | 1 Hour | 2 Hours | 3 Hours |
| 1. REST PAIN-Constant uninterrupted pain without stimulus | | | | | | | | | | | | |
| A. Ketamine 0.5% | 64.7 | 82.4 | 61.8 | 0 | | | 100 | 0 | 0 | 91.2 | 82.4 | 58.8 |
| B. Amitriptylline 0.05% | 32.4 | 50.0 | 32.4 | 5.9 | | | 79.4 | 11.8 | 8.8 | 52.9 | 50.0 | 32.4 |
| C. Guanethidine 0.05% | 5.9 | 8.8 | 2.9 | 11.8 | | | 76.4 | 8.8 | 17.6 | 14.7 | 8.8 | 2.9 |
| D. A + B | 82.4 | 97.1 | 97.1 | 0 | | | 100 | 0 | 0 | 97.1 | 97.1 | 97.1 |
| E. A + C | 79.4 | 88.2 | 82.4 | 0 | | | 100 | 0 | 0 | 94.1 | 88.2 | 82.4 |
| F. Placebo | 0 | 0 | 0 | 94.1* | 0 | 0 | 2.9 | 0 | 0 | 0 | | |

-continued

Total number of patients treated: 34 patients
Average age of patients treated: 52 years of age

| Treatment | Percentage Patients with >50% Pain Relief | | | Percentage Patients with 0 Pain Relief | | | Time of Onset of Pain Relief (Patient Percentage) | | | Duration of >50% Pain Relief (Patient Percentage) | | |
|---|---|---|---|---|---|---|---|---|---|---|---|---|
| | At 5 Minutes | At 2 Hours | At 3 Hours | At 5 Minutes | At 2 Hours | At 3 Hours | 5 Minutes | 10 Minutes | >15 Minutes | 1 Hour | 2 Hours | 3 Hours |
| 2. ALLODYNIA | | | | | | | | | | | | |
| A. Ketamine 0.5% | 79.4 | 82.4 | 82.4 | 2.9 | | | 91.2 | 5.9 | 2.9 | 82.4 | 82.4 | 82.4 |
| B. Amitriptylline 0.05% | 8.8 | 11.8 | 5.9 | 47.1 | | | 35.3 | 2.9 | 58.8 | 11.8 | 11.8 | 5.9 |
| C. Guanethidine 0.05% | 0 | 0 | 0 | 67.6 | | | 17.6 | 8.8 | 73.5 | 0 | 0 | 0 |
| D. A + B | 88.2 | 91.2 | 91.2 | 0 | | | 100.0 | 0 | 0 | 91.2 | 91.2 | 91.2 |
| E. A + C | 79.4 | 85.3 | 85.3 | 2.9 | | | 91.2 | 5.9 | 2.9 | 82.4 | 82.4 | 82.4 |
| F. Placebo | 0 | 0 | 0 | 94.1* | | | 0 | 0 | 2.9 | 0 | 0 | 0 |

*5.9% developed minimal statistically significant pain relief.

Topical Compositions Study: Summary of Results

| Rest Pain | Onset of Pain Relief (Patient Percentage) | | | >50% Pain Relief (Patient Percentage) | | | Duration of >50% Pain Relief (Patient Percentage) | | |
|---|---|---|---|---|---|---|---|---|---|
| | 5 Min. | 10 Min. | >15 Min. | 5 Min. | 2 Hours | 3 Hours | 1 Hour | 2 Hours | 3 Hours |
| A. Ketamine 0.5% | 100 | 0 | 0 | 64.7 | 82.4 | 61.8 | 91.2 | 82.4 | 58.8 |
| B. Amitriptylline 0.05% | 79.4 | 11.8 | 8.8 | 32.4 | 50.0 | 32.4 | 52.9 | 50.0 | 32.4 |
| C. Guanethidine 0.05% | 76.4 | 8.8 | 17.6 | 5.9 | 8.8 | 2.9 | 14.7 | 8.8 | 2.9 |
| A + B | 100 | 0 | 0 | 82.4 | 97.1 | 97.1 | 97.1 | 97.1 | 97.1 |
| A + C | 100 | 0 | 0 | 79.4 | 88.2 | 82.4 | 94.1 | 88.2 | 82.4 |
| Placebo | 0 | 0 | 2.9 | 0 | 0 | 0 | 0 | 0 | 0 |

| Allodynia | Onset of Pain Relief (Patient Percentage) | | | >50% Pain Relief (Patient Percentage) | | | Duration of >50% Pain Relief (Patient Percentage) | | |
|---|---|---|---|---|---|---|---|---|---|
| | 5 Min. | 10 Min. | >15 Min. | 5 Min. | 2 Hours | 3 Hours | 1 Hour | 2 Hours | 3 Hours |
| A. Ketamine 0.5% | 91.2 | 5.9 | 2.9 | 79.4 | 82.4 | 82.4 | 82.4 | 82.4 | 82.4 |
| B. Amitriptylline 0.05% | 35.3 | 2.9 | 58.8 | 8.8 | 11.8 | 5.9 | 11.8 | 11.8 | 5.9 |
| C. Guanethidine 0.05% | 17.6 | 8.8 | 73.5 | 0 | 0 | 0 | 0 | 0 | 0 |
| A + B | 100 | 0 | 0 | 88.2 | 91.2 | 91.2 | 91.2 | 91.2 | 91.2 |
| A + C | 91.2 | 5.9 | 2.9 | 79.4 | 85.3 | 83.3 | 82.4 | 82.4 | 82.4 |
| Placebo | 0 | 0 | 2.9 | 0 | 0 | 0 | 0 | 0 | 0 |

Discussion

The following points warrant additional comment.

I. Significant Pain Relief and Duration of Relief

A. Rest Pain

A total of 97% of the study patients achieved greater then a 50% reduction in their rest pain following application of lecithin matrix gel containing the combination of 0.5% ketamine plus 0.05% amitriptylline at two and three hours following application.

The 0.5% ketamine composition alone produced significant pain relief in 82% of patients at 2 hours and 62% at 3 hours.

The 0.05% guanethidine composition was effective only when combined with 0.5% ketamine, providing 88% of the patients with significant pain relief lasting two hours or more. 82% of these patients achieved greater than three hours of almost total pain relief.

The respective significant pain relief percentages for the 0.05% amitriptylline composition were 50% at 2 hours and 32% at 3 hours.

In those patients who had placebo topical composition applied, none demonstrated more than a 20% pain reduction at any of the test measurement intervals, which did not meet the criteria of significant (>50%) pain relief.

The duration of the significant pain relief was 3 hours or more in 97% of the patients treated with 0.5% topical ketamine plus 0.05% ketamine.

This was compared to only 59% of patients with significant pain relief lasting 3 hours or more treated with 0.5% ketamine alone in a composition and 32% of patients treated with 0.05% amitriptylline alone in a composition.

B. Allodynia—(Pain Upon Light Touch)

Application of 0.5% ketamine alone resulted in 82% of these patients experiencing significant pain relief at two and three hours.

Adding 0.05% amitriptylline to ketamine was advantageous in that 91% of the patients experienced significant pain relief at two and three hours.

There was no apparent advantage to adding guanethidine to the ketamine since 85% of these patients reported significant pain relief at two and three hours an insignificant difference from the 82% with ketamine alone.

0.05% guanethidine alone and placebo compositions were statistically ineffective for relief of allodynia. None of these patients experienced significant pain relief.

Once developing a significant reduction of pain, 82% of the allodynia patients who were treated with the 0.5% ketamine or 0.5% ketamine plus 0.05% guanethidine compositions, maintained that level of pain relief for greater than three hours. However, 91% of patients treated with 0.5% ketamine plus 0.05% amitriptylline experienced three hours of significant pain relief. This compared to only 6% of patients treated with the 0.05% topical amitriptylline alone.

II. Onset of Significant Pain Relief

All of the rest pain and allodynia patients treated with 0.5% ketamine or 0.5% ketamine plus 0.05% guanethidine or 0.05% amitriptylline experienced onset of significant pain relief within five minutes of application. 0.05% amitriptylline composition had a slower onset, with 80% of rest pain patients and only 35% of allodynia patients experiencing relief in the first five minutes after application of the topical composition. Onset of significant pain relief was over 15 minutes in 60% of the allodynia patients.

III. Statistical Analysis

Our analysis[1] revealed this treatment to be effective equally in diabetic peripheral neuropathy, idiopathic peripheral neuropathy, peripheral neuropathy in patients with AIDS, and patients with other mixed types of pain, especially sympathetically mediated pain. No significant differences were found related to the age or sex of the patients.

[1] Bruce M. Frome, MD "Raw Data and Statistical Analysis from Clinical Trials Comparing Efficacy of Topical Compositions containing Therapeutically Active Agents on Relief of Sympathetically Mediated Pain". September 1995: Un-published paper.

Conclusions:

1. Topical compositions containing 0.5% ketamine, an N-methyl-D-aspartate (NMDA) receptor antagonist, are effective for use in the treatment and relief of rest pain and aliodynia due to nerve injury (SMP).

2. Topical compositions containing 0.05% amitriptylline, an example of an anticholinergic agent, are effective for use in the treatment and relief of rest pain but ineffective for heating allodynia secondary to nerve injury (SMP).

3. Topical compositions containing 0.05% guanethidine, a sympathetic blocking agent, are effective in reducing the intensity of rest pain due to nerve energy (SMP). However, 0.05% guanethidine was ineffective in the relief of the allodynia type pain due to nerve injury.

4. Topical compositions containing both 0.5% ketamine and 0.05% amitriptylline proved to be the most effective for the relief of pain due to nerve injury (SMP) after comparing efficacy of 0.5% topical ketamine, 0.05% topical guanethidine, and 0.05% topical amitriptylline, individually and in combinations. Almost all patients treated with the 0.5% ketamine/0.05% amitriptylline composition combination in lecithin composition exhibited rapid and almost complete relief of all pain that lasted greater than three hours.

5. Administered separately, 0.5% topical ketamine compositions were the most effective offering all patients rapid, prolonged and significant pain relief from pain due to nerve injury (SMP). 0.05% amitriptylline topically administered separately in a composition was less effective than ketamine. 0.05% topical guanethidine administered separately in a composition was the least effective of the three active ingredients studied.

6. Time of onset of significant pain relief was less than five minutes in almost all of patients studied when 0.5% topical ketamine was part of the formula. Duration of onset was longer when 0.05% topical amitriptylline was used separately without topical ketamine. 0.05% topical guanethidine compositions had the longest onset of action over fifteen minutes after topical application, in the majority of patients studied.

7. No side effects attributable to the topical compositions were demonstrated by any of the patients studied. Nevertheless, low blood pressure or a history of vascular headaches is a relative contraindication to the use of topical guanethidine.

8. Due to its convenience, simplicity of self application, lack of side effects, ease of preparation, and low cost, the use of topical regional treatment is a valuable addition to the treatment protocol of nerve injury pain (SMP).

Conclusions, Ramifications, and Scope

Accordingly, it can be seen that we have provided a method of preparation of compositions resulting in a relatively simple method of treating pain, regardless of cause, and including all forms of peripheral neuropathy, in patients of either sex. The method of preparation utilizes therapeutically active agents prepared in suitable bases then applied periodically to the skin areas affected by such pain.

The therapeutically active agents include three classes of drugs: NMDA receptor antagonists, anticholinergic agents and sympathetic blocking agents, as well as combinations of two or more of these. The method provides a rapid onset of significant pain relief which lasts significantly greater than 2 hours in the patients studied. The topical compositions are generally non-toxic and have minimal non-serious side effects. Specifically, no habit forming or addicting medications are used. The topical compositions can be self administered safely at home or administered by a care giver in any locale.

Although the description above contains specific examples of ketamine, an NMDA antagonist, used at its most effective concentration of 0.5%, it was also found in clinical trials to be safe and effective when prepared with the dosage between 0.05% to 2% of the topical composition.

Although the description above contains specific examples of amitriptylline, an anticholinergic agent, used at its most effective concentration of 0.05%, it was also found in clinical trials to be safe and effective when prepared with the dosage between 0.01% to 0.1% of the topical composition.

Although the description above contains specific examples of guanethidine, a sympathetic blocking agent, used at its most effective concentration of 0.05%, it was also been found in clinical trials to be safe and effective when prepared with the dosage between 0.01% to 0.1% of the topical composition.

Although the description above contains many specificies, these should not be construed as limiting the scope of the invention but as merely providing illustrations of some of the presently preferred embodiments of this invention. Various other embodiments and ramifications are possible within its scope.

Thus the scope of the invention should be determined by the appended claims and their legal equivalents, rather than by the examples given.

That which is claimed is:

1. A method for achieving regional pain relief, said method comprising topically applying a mixture comprising a combination of one or more NMDA receptor antagonists and one or more tricyclic antidepressants in a topical vehicle to a subject in need thereof.

2. The method of claim 1, wherein the NMDA receptor antagonist is ketamine.

3. The method of claim 1, wherein said mixture comprises a combination of the NMDA receptor antagonists ketamine and dextromethorphan.

4. The method of claim 1, wherein the NMDA receptor antagonist is ketamine and the tricyclic antidepressant is amitriptyline.

5. The method of claim 1, wherein the topical vehicle is selected from the group consisting of cocoa butter, aloe vera gel, aquafor, petroleum jelly, lecithin and cream.

6. The method of claim 1, wherein the topical vehicle is lecithin matrix gel.

7. A method for preparing a therapeutic composition for topical use to achieve regional pain relief, said method comprising combining one or more NMDA receptor antagonists and one or more tricyclic antidepressant with one or more suitable topical vehicles, wherein the topical vehicle is selected from the group consisting of cocoa butter, aloe vera gel, aquafor, petroleum jelly, lecithin, cream, lecithin matrix gel and combinations of any two or more thereof.

8. The method of claim 7, wherein the NMDA receptor antagonist is ketamine.

9. The method of claim 7, wherein the tricyclic antidepressant is amitriptyline.

10. The method of claim 7, wherein the NMDA receptor antagonist is ketamine and the tricyclic antidepressant is amitriptyline.

11. A composition comprising an amount of (i) one or more NMDA receptor antagonists and (ii) one or more tricyclic antidepressants effective for the relief of regional pain, and a suitable topical vehicle.

12. The composition according to claim 11, wherein the NMDA receptor antagonist is ketamine.

13. The composition according to claim 11, wherein the tricyclic antidepressant is amitriptyline.

14. The composition according to claim 11, wherein the NMDA receptor antagonist is ketamine and the tricyclic antidepressant is amitriptyline.

15. The composition according to claim 11, wherein the topical vehicle is selected from the group consisting of cocoa butter, aloe vera gel, aquafor, petroleum jelly, lecithin, cream and lecithin matrix gel.

* * * * *